United States Patent
Sakamoto et al.

(10) Patent No.: US 10,123,816 B2
(45) Date of Patent: *Nov. 13, 2018

(54) ARTHROENDOSCOPICAL SURGICAL METHOD USING ULTRASONIC TREATMENT TOOL

(71) Applicant: OLYMPUS CORPORATION, Tokyo (JP)

(72) Inventors: Takamitsu Sakamoto, Hachioji (JP); Chie Onuma, Tama (JP); Kiichiro Sawada, Hachioji (JP); Ken Fujisaki, Sagamihara (JP); Kazuhiro Yoshida, Sagamihara (JP); Satoshi Takekoshi, Hachioji (JP); Sohei Ueda, Tokyo (JP); Yasuo Tanigami, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 271 days.

This patent is subject to a terminal disclaimer.

(21) Appl. No.: 15/082,519

(22) Filed: Mar. 28, 2016

(65) Prior Publication Data
US 2017/0273708 A1    Sep. 28, 2017

(51) Int. Cl.
*A61B 17/32* (2006.01)
*A61B 17/06* (2006.01)

(52) U.S. Cl.
CPC ........... *A61B 17/320068* (2013.01); *A61B 17/06166* (2013.01); *A61B 2017/320072* (2013.01); *A61B 2017/320084* (2013.01)

(58) Field of Classification Search
CPC ...... A61B 17/320068; A61B 17/06166; A61B 2017/320084; A61B 2017/320072
USPC ................................. 600/437–469
See application file for complete search history.

(56) References Cited

U.S. PATENT DOCUMENTS

2015/0297073 A1* 10/2015 Nguyen ................. A61B 1/317
                                                  600/103
2017/0367727 A1* 12/2017 Sakai ............. A61B 17/320068

* cited by examiner

*Primary Examiner* — Sanjay Cattungal
(74) *Attorney, Agent, or Firm* — Oliff PLC (57) ABSTRACT

In an arthroendoscopical surgical method, a resection target area, and a freshening treatment area which becomes repair surfaces with bleeding, are identified, and a resection line and a freshening line are drawn on a tear site in a meniscus, which is emphasized by fluorescence with use of a fluorescent medicine under excitation light. Using an ultrasonic treatment tool and an arthroscope, the resection target area is resected by a probe which generates ultrasonic vibrations, based on the resection line and freshening line under visible-light illumination. Thus, an inclined resection surface is formed, and planar repair surfaces with bleeding are joined and repaired.

9 Claims, 10 Drawing Sheets

FIG. 8B ant ARTHROENDOSCOPICAL SURGICAL METHOD USING ULTRASONIC TREATMENT TOOL

FIELD OF THE INVENTION

The present invention relates to an arthroendoscopical surgical method of treating a meniscus by using an ultrasonic treatment tool under arthroendoscopy.

DESCRIPTION OF THE RELATED ART

There is known a surgical operation which is generally called arthroendoscopical surgery. In the arthroendoscopical surgery, two or so small holes (external portals) are opened in the skin near an articulation. A rigid scope, which will serve as an arthroscope, and a therapeutic device, are inserted from the external portals (or portals). Treatment is performed while confirming video which is displayed on a monitor in a state in which the inside of the articulation is filled with perfusion water for articulation surgery.

For example, as disclosed in patent document 1 (US2015/0297073), the arthroendoscopical surgery is applicable to a surgical operation for administering surgical treatment to a meniscus. Endoscopical surgical methods using arthroscopes for menisci are generally classified into resection surgery which resects an injured denatured part of a meniscus, and repair surgery which repairs a denatured part. Either resection alone or repair is selected in consideration of a diagnosis result based on various conditions such as a form of tear, a part of tear, or the presence/absence of a blood flow in an injured part of a meniscus.

When the need for repair is determined, it is necessary to rasp the surface of the injured part by using a file or the like, and to form repair surfaces which are freshened to cause microbleeding. The meniscus is a white tissue, and the visibility of the state of the injured part is poor under visible-light illumination. Meanwhile, it is required to exactly grasp the range of a damage, even with respect to a damage to an inner part of the meniscus, which is hardly viewed from the outside, such as a horizontal tear.

In addition, at a time of freshening, a rasp, a shaver, or the like is used as a conventional treatment tool which enables biological repair by causing microbleeding to occur in a tissue. However, the efficiency of hemorrhage from an end face of a meniscus is poor, and it is difficult to visually recognize whether a blood flow is occurring or not. Moreover, as regards repair surfaces on which repair treatment is performed, the angle of abutment surfaces and the smoothness, which enable close contact between the repair surfaces, are required.

BRIEF SUMMARY OF THE INVENTION

According to an embodiment of the invention, an arthroendoscopical surgical method using an ultrasonic treatment tool includes an identifying step of identifying a tear site of a meniscus which is observed by an arthroscope; an imaging step of administering a fluorescent medicine to a blood flow of the meniscus through a vein, and imaging the meniscus in which the blood flow is displayed with emphasis under excitation light; a confirmation step of confirming whether the tear site in an image of the imaged meniscus reaches a vascular area; a step of confirming a blood vessel in a depth direction from a tear surface of the tear site in the image of the imaged meniscus; a step of forming mutually opposed planar repair surfaces by cutting the tear surfaces of the tear site in the depth direction by an ultrasonic treatment tool, such that bleeding occurs from the blood vessel in an inside of the meniscus to the tear surfaces; and a repair step of joining and suturing the repair surfaces formed in the step of forming the repair surfaces.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE PREFERRED EMBODIMENT

Hereinafter, an embodiment of the present invention will be described in detail with reference to the accompanying drawings.

Figure 1:
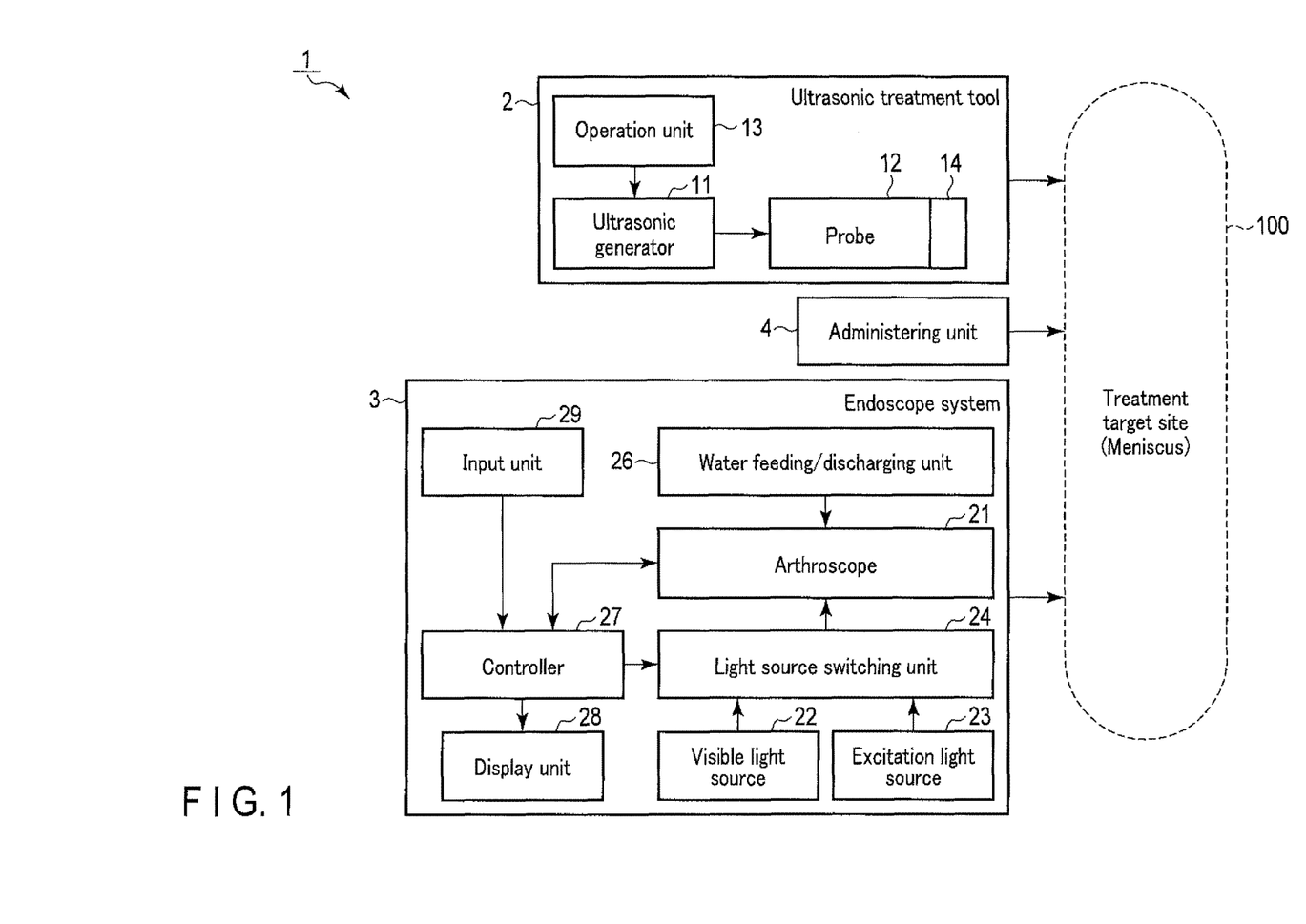
FIG. 1 is a view illustrating a configuration example of a surgery system including an ultrasonic treatment tool for implementing an arthroendoscopical surgical method according to an embodiment.

FIG. 1 illustrates a configuration example of a surgery system including an ultrasonic treatment tool for implementing an arthroendoscopical surgical method according to the embodiment. In the embodiment below, a description is given on the assumption that a treatment target site 100 of arthroendoscopical surgery is a meniscus by way of example.

A surgery system 1 of the present embodiment is composed of an ultrasonic treatment tool 2, an endoscope system 3 including an arthroscope, and an administering unit 4 configured to administer a fluorescent medicine.

The ultrasonic treatment tool 2 includes an ultrasonic generator 11 configured to generate ultrasonic vibrations by an ultrasonic vibration element (e.g. a piezoelectric element); a probe 12 configured to transmit ultrasonic vibrations and perform cutting treatment of a treatment target site; and an operation unit 13 configured to execute driving control of the ultrasonic generator 11, and to on/off operate the generation of ultrasonic vibrations.

The probe 12 is an elongated rod-shaped member which extends in a longitudinal axis direction and has a diameter of about 2 mm to 4 mm, and includes a distal end portion and a proximal end portion. The proximal end portion of the probe 12 is coupled to the ultrasonic generator 11, and a treatment unit 14 is provided on the distal end portion. The probe 12 transmits ultrasonic vibrations to the treatment unit 14, and performs cutting treatment, with the treatment unit 14 being put in contact with the meniscus 100. The treatment unit 14 has, for example, a distal end shape of a rasp, or a hook shape with at least one projection. It is possible to prepare in advance a plurality of treatment units 14 which are bent at different angles in a range of arbitrary angles of, e.g. 5° to 30°, relative to the longitudinal axis of the probe 12. A probe with a suitable angle is properly selected based on the treatment content which is administered to the treatment target site 100, and the positional relationship between the portal for inserting the treatment unit 14 and the location of treatment. In the meantime, the rasp is a tool for a surgical operation, which includes a distal end portion having a surface with a plurality of projections or with raised file teeth, and is used for smoothing, grinding-in, or cutting of a tissue.

This ultrasonic treatment tool 2 performs resection by ultrasonic vibrations, that is, mechanical resection and resection by frictional heat by minute sliding movement, by putting the treatment unit 14, which is provided at the distal end of the probe 12 that generates ultrasonic vibrations, into contact with the meniscus 100 that is the treatment target site. The ultrasonic treatment tool 2 can adjust the amount of cutting, in accordance with the pressure of pushing or the time of pushing of the treatment unit 14 upon the meniscus 100.

The ultrasonic treatment tool 2 performs mechanical cutting by minute sliding movement by ultrasonic vibrations applied to the probe that is supported at one end to the ultrasonic element. Thus, the amount of cutting can be adjusted in accordance with the degree (pushing pressure) of strength of pushing the distal-end treatment unit 14 upon the treatment part. Specifically, if the degree of contact is weak, the amount of cutting is small, and smoothing or fine cutting of the surface of the treatment target site is realized. If the degree of contact is strong, the amount of cutting increases. Accordingly, with the degree of cutting by a surgeon being reflected, efficient cutting, abscission, etc. are realized.

The endoscope system 3 includes an arthroscope 21 which is composed of a rigid scope that is a kind of endoscope; a visible light source 22 serving as an illumination light source, which is configured to radiate visible-light illumination; an excitation light source 23 configured to radiate excitation light (to be described later); a light source switching unit 24 configured to effect switching between the visible light and the excitation light, which are made incident on the arthroscope 21; a water feeding/discharging unit 26 configured to feed, discharge or perfuse perfusion water for articulation surgery, around the region including the meniscus 100 of the treatment target site; a controller 27 configured to control the entirety of the endoscope system 3; a display unit 28 configured to display surgery information including a imaged surgery condition; and an input unit 29 such as a keyboard or a touch panel. The present embodiment is configured such that the water feeding/discharging unit 26 feeds/discharges perfusion water for articulation surgery to/from the treatment site through the arthroscope 21. However, such a configuration may be adopted that the perfusion water for articulation surgery is fed/discharged from the ultrasonic treatment tool 2.

In addition, in the present embodiment, when the meniscus 100 is treated, a blood flow is visualized with fluorescence under infrared observation (IR observation), and a resection line 61 shown in FIG. 4B and FIG. 4C (to be described later) is determined. Here, a fluorescent medicine, in which infrared is easily absorbed, for instance, indocyanine green (ICG) (hereinafter referred to as "ICG"), is administered to a blood flow, and blood vessel or blood flow information is displayed with emphasis by using infrared which has good transmissivity. In this embodiment, as the fluorescent medicine, ICG is described by way of example. However, other generally used fluorescent medicines may be used, and the fluorescent medicine is not limited to ICG. The administering unit 8 shown in FIG. 1 is a syringe, and a fluorescent medicine is administered by intravenous injection or local injection (articular injection; indirect injection into a soft tissue).

The fluorescent display by the indocyanine green is used, for example, for a liver function test, a cardiovascular function test, or cerebral angiography, and no chemical change is suffered in the body. In addition, the concentration transition in the plasma decreases exponentially until about 15 minutes after administration, and then the decrease becomes gentle, and the indocyanine green quickly disappears from the plasma.

Figure 2:
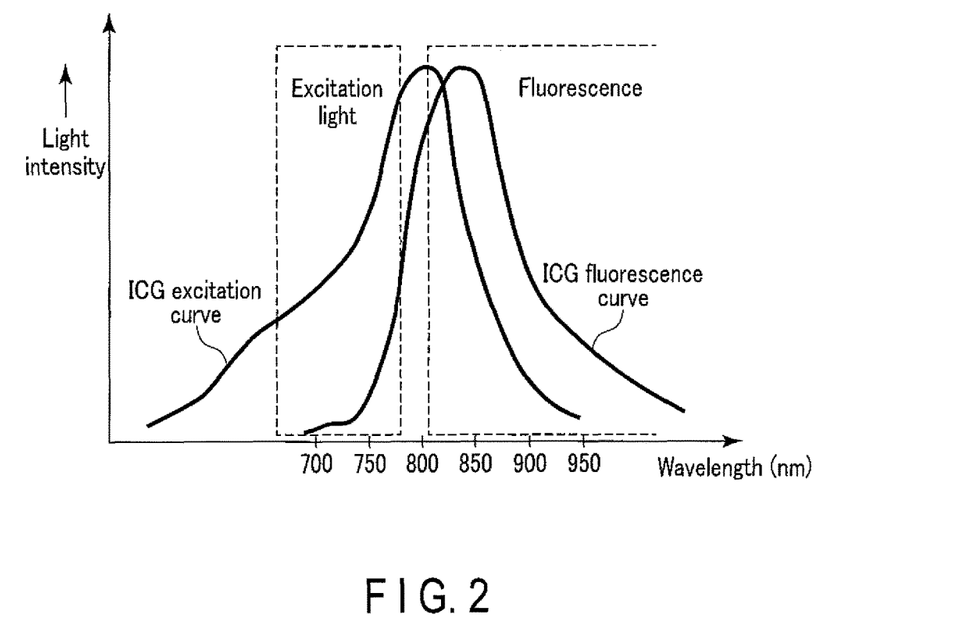
FIG. 2 is a view illustrating the relationship between wavelength and light intensity in excitation light and fluorescence.

As indicated by publicly known characteristics shown in FIG. 2, if the ICG is excited by irradiation of excitation light (ICG excitation curve) of near-infrared with wavelengths of 670 to 790 nm, fluorescence of near-infrared (ICG fluorescence curve) occurs with a peak wavelength of 835 nm which is longer than the wavelengths of 670 to 790 nm. By this fluorescence, a deep part of a living body (about 2 to 3 mm) can be observed. However, the fluorescence of the ICG is not directly visible to the human eye. Thus, by using a camera (CCD) which can image an object at this wavelength band, the fluorescence can be observed as an image.

In addition, in the present embodiment, the configuration in which the light source can be switched by the light source switching unit 24 is included. During the observation, the same observation object can be observed while switching is made between infrared and visible light for use in normal observation. Furthermore, in the embodiment, a touch panel is disposed on the display screen of the display unit 28, and a publicly known function is provided which enables drawing of a line on the screen by an input by the touch of a fingertip or pen, or by a cursor movement by a mouse. For example, while a surgeon is observing the meniscus on the fluorescence screen, the surgeon traces over the screen by the fingertip in order to distinguish a specific area where fluorescence occurs partly. Thereby, a line is drawn along the tracing. If this screen is changed to an observation screen with illumination by visible light, a transition occurs to the state in which the line is drawn over the image of the meniscus. If this line is set as a resection line for resection, an area to be resected can easily be determined.

Figure 3A:
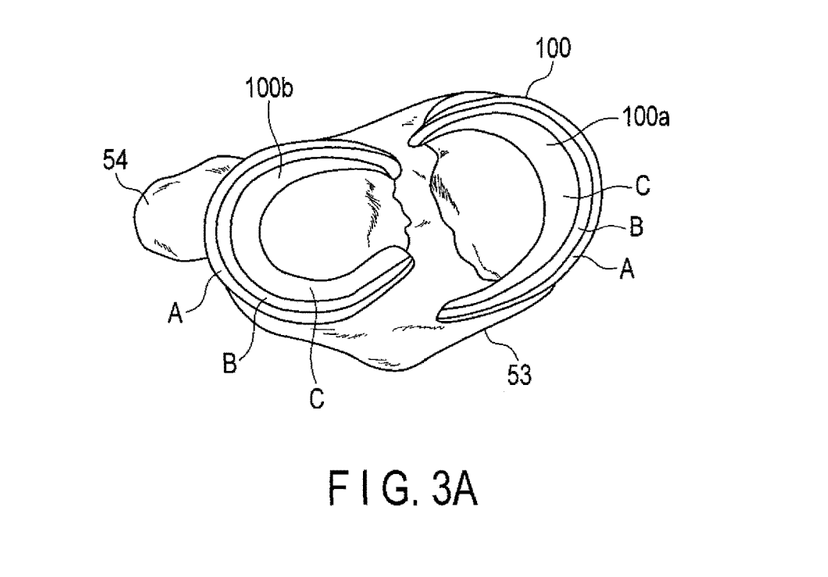
FIG. 3A is an external appearance view of a meniscus on the tibia, as viewed from the femur side.
Figure 3B:
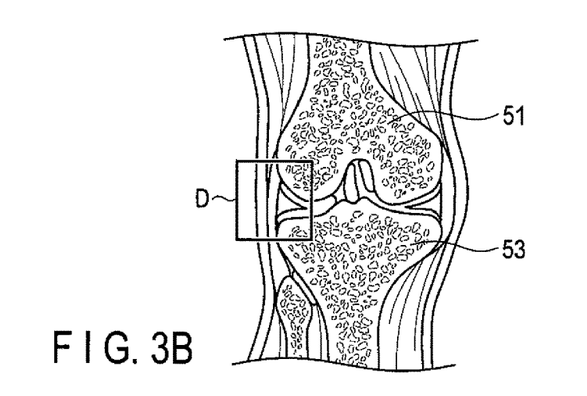
FIG. 3B is a view illustrating a cross section of a meniscus in a state in which the meniscus lies between the femur and tibia.
Figure 3C:
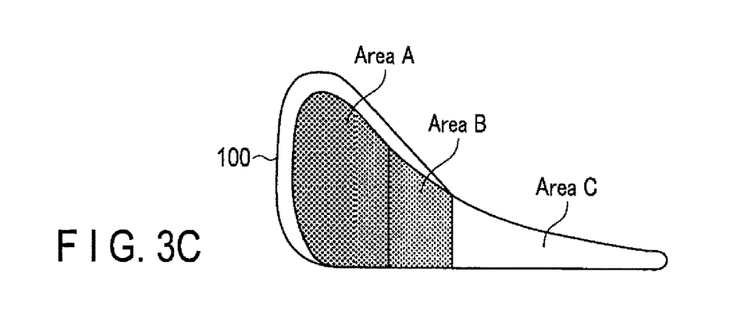
FIG. 3C is a view illustrating a cross section of the meniscus in a part D in FIG. 3B.

Here, referring to FIG. 3A, FIG. 3B and FIG. 3C, a description is given of the meniscus 100, the meniscus 100 to which a fluorescent medicine is administered, and a resection area of the meniscus 100. FIG. 3A is an external appearance view of the meniscus 100 on the tibia 53, as viewed from the femur 51 side. FIG. 3B is a view illustrating a cross section of the meniscus 100 in a state in which the meniscus 100 lies between the femur 51 and tibia 53. FIG. 3C is a view illustrating a cross section of the meniscus 100 in a part D in FIG. 3B.

As illustrated in FIG. 3A, the meniscus 100 is composed of two C-shaped cartilage-like tissues, which are disposed to be opposed to each other from both sides, namely the medial side and lateral side, like the shape of numeral "8", between the femur 51 and tibia 53 of the knee joint of the leg. The meniscus 100 functions as a cushion and a stabilizer. The meniscus 100 is composed of a medial meniscus 100a and a lateral meniscus 100b. As illustrated in FIG. 3B, the upper surfaces of these menisci 100 extend along spherical surfaces of the femur 51, and the lower surfaces thereof extend along planar surfaces of the tibia 53. Thus, as illustrated in FIG. 3C, in the cross section, the meniscus 100 has a less thickness on the inside, and a greater thickness toward the periphery.

On the outer peripheral side of the meniscus 100, there is a dense blood flow area A [vascular area: dense blood flow area] where many blood flows (blood vessels) exist. Toward the inside of the arc, there is an area B [vascular area: sparse blood flow area] where fewer blood flows than in the area A exist. In the inner side of the area B, there is an area C [avascular area: no-blood-flow area] where no blood flow exists. When the meniscus 100 is injured, the area A and area B, in which blood is flowing, can be regenerated. On the other hand, when the area C of the no-blood-flow area with no blood flow is injured, the area C cannot be regenerated, and thus only resection treatment is performed on the area C.

Figure 3D:
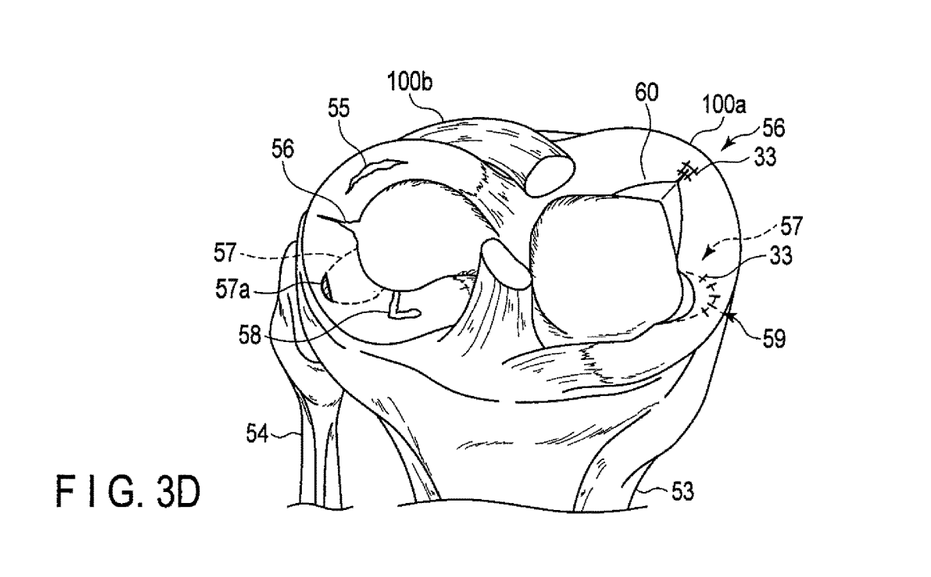
FIG. 3D is a view for describing damages occurring in the meniscus, and the state of the meniscus after resection and repair treatment.

Here, FIG. 3D illustrates typical damages occurring in the lateral meniscus 100b, and the state of the medial meniscus 100a after resection treatment. In general terms, the lateral meniscus 100b includes a longitudinal tear 55 in which an inner cartilage tissue is torn in an up-and-down direction (longitudinally) along the longitudinal direction; a transverse tear 56 in which a tissue is torn like a cut from the inside toward the outside; a horizontal tear 57 in which an inner part is torn horizontally; and a flap tear 58 in which a tissue is torn longitudinally in an L shape. Resection treatment is performed on any of these damages, if the damage is a tear existing in the no-blood-flow area C.

However, if the damage is the horizontal tear 57 which reaches the area A or area B, and in which a blood flow (blood vessel) is visually recognizable, a combination of resection treatment and repair treatment is performed, and a repair treatment part 59 is formed. Similarly, if the damage is the transverse tear 56 in which a blood flow (blood vessel) is visually recognizable, a combination of resection treatment and repair treatment is performed, and a repair treatment part 60 is formed.

To begin with, a description is given of ultrasonic resection treatment and repair(suture) treatment on a tear site.

As a first example, a description is given of a resection method at a time when the horizontal tear 57, which reaches the blood flow area A of the meniscus 100, has occurred.

Figure 4A:
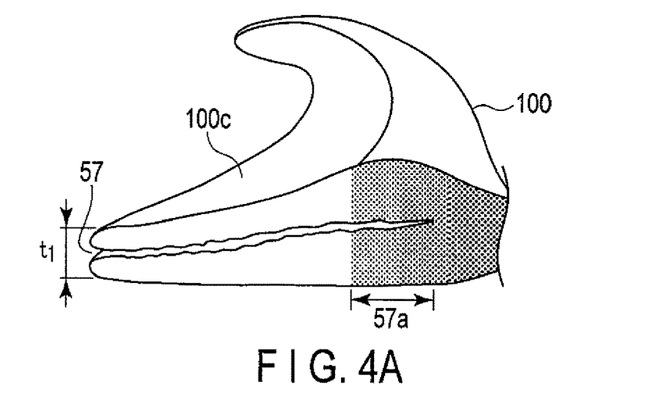
FIG. 4A is a cross-sectional view which conceptually illustrates a state in which a horizontal tear occurred in the meniscus.
Figure 4B:
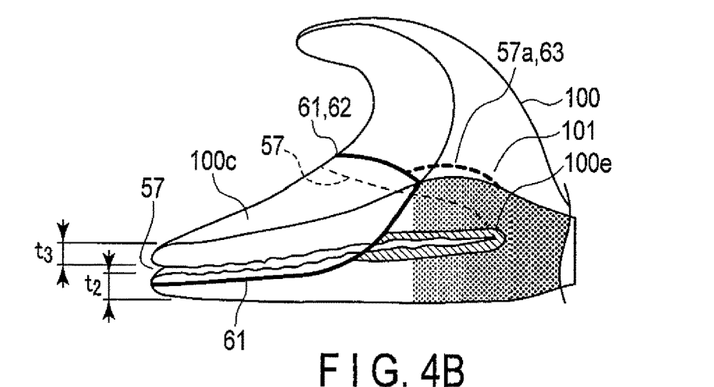
FIG. 4B is a cross-sectional view which conceptually illustrates a state in which a resection line or an imaginary resection line is provided on the horizontal tear.
Figure 4C:
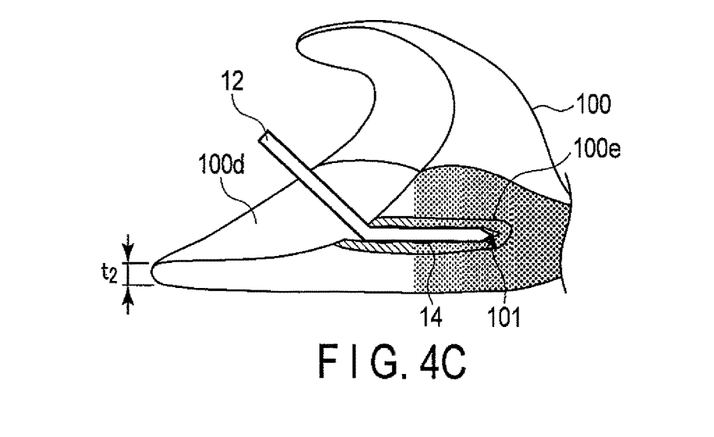
FIG. 4C is a cross-sectional view which conceptually illustrates a treatment state in which a tear site is resected by the ultrasonic treatment tool, and repair surfaces are freshened.
Figure 4D:
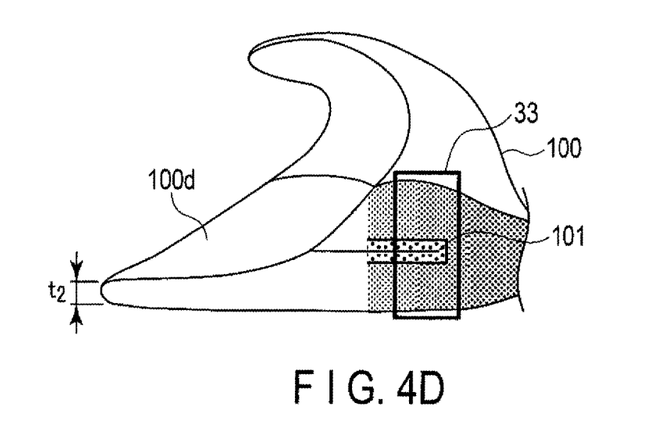
FIG. 4D is a cross-sectional view which conceptually illustrates a state in which repair treatment is performed.
Figure 5:
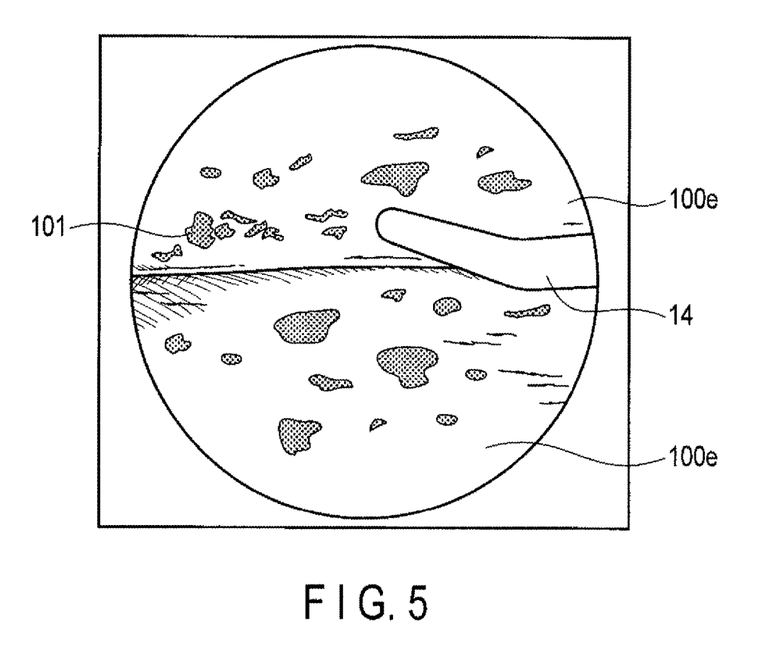
FIG. 5 is a view illustrating a state of freshening treatment of rasping surfaces of a damaged part of the meniscus by the ultrasonic treatment tool, and microbleeding is caused to occur.

FIG. 4A is a cross-sectional view which conceptually illustrates a state in which the horizontal tear 57 occurred in the meniscus 100. FIG. 4B is a cross-sectional view which conceptually illustrates a state in which a resection line 61 or an imaginary resection line 62 is provided on the horizontal tear 57. FIG. 4C is a cross-sectional view which conceptually illustrates a treatment state in which a tear site is resected by the ultrasonic treatment tool, and repair surfaces are freshened. FIG. 4D is a cross-sectional view which conceptually illustrates a state in which repair treatment is performed. FIG. 5 is a view for describing treatment of freshening repair surfaces in the horizontal tear 57 of the meniscus 100.

As illustrated in FIG. 4A, it is assumed that a horizontal tear 57 occurs in the meniscus 100, the horizontal tear 57 extending from the area C of no blood flow toward the inside, and entering the area A of the vascular area shown in FIG. 3D.

Probing (identification of tear site) is performed for setting a treatment target area of the meniscus 100.

To begin with, using the administering unit 8, a fluorescent medicine (ICG) is administered into a vein of a patient. Then, the arthroscope 21 is inserted from a portal provided in the knee, and excitation light is radiated from the excitation light source 23 to the meniscus 100. By the radiation of excitation light, the fluorescent medicine, which is diffused in the meniscus 100, emits fluorescence. Since the density of the fluorescent medicine becomes higher as the number of blood flows (blood vessels) is greater, this fluorescence becomes stronger where the number of blood flows is greater, and the fluorescence becomes weaker where the number of blood flows is smaller. Accordingly, light emission is strong in the area A of the meniscus 100 displayed on the display unit 28, and light emission becomes weaker toward the area B. Further, substantially no light is emitted in the area C with no blood flow. Thus, the horizontal tear 57 shown in FIG. 4A (freshening line 57a in FIG. 3D) can be confirmed by visually recognizing the blood flows (blood vessels) in the depth direction from the tear surface by IR observation.

Next, a description is given of marking of a line for performing resection and a line for performing freshening treatment.

The surgeon selects either a first marking method or a second marking method. The first marking method is a direct drawing method in which the resection line 61 is marked by abutting the treatment unit 14, which generates ultrasonic vibrations, upon the meniscus 100. The second marking method is an imaginary drawing method in which the surgeon traces over the touch panel by the fingertip while viewing an IR image, thereby marking the imaginary resection line 62 on the display screen.

In the first marking method, the surgeon puts the treatment unit 14 of the ultrasonic treatment tool 2, which is caused to generate ultrasonic vibrations, into contact with the inner side end of the meniscus 100, while viewing the IR image under excitation light. Then, the surgeon moves the treatment unit 14 to a location in front of the blood flow area A (vascular area), and directly makes marking on the meniscus 100 (makes a scar in the shape of consecutive dots or a thread), thus drawing the resection line 61 and identifying a resection target area 100c. At this time, the resection line 61 is drawn in a range exceeding the horizontal tear 57. Next, a freshening line 57a is marked on a position of the horizontal tear 57 in the blood flow area A, and a freshening treatment area is set. In addition, in FIG. 4B, the freshening treatment area is a planarized repair surface (to be described later), and microbleeds occur on this surface. In these markings, it is preferable that the resection target area 100c and freshening treatment area have different shapes so as to be visually distinguishable.

In the second marking method, the surgeon traces over the touch panel of the display unit 28, which is subjected to sterilization treatment, by the fingertip, while viewing the blood flows (blood vessels) in the depth direction from the tear surface by the IR observation under excitation light. Thus, by drawing an imaginary resection line 62 on the meniscus image on which the blood flow is displayed with emphasis, as well as an imaginary freshening line 63 for freshening treatment, the surgeon identifies a three-dimensional resection target area 100c and freshening treatment area 100e.

The setting of the imaginary resection line 62 and imaginary freshening line 63 can be realized by mounting application software in the controller 27. At a time of drawing, the imaginary resection line 62 and imaginary freshening line 63 are drawn by being associated with the position information of the meniscus 100 on the screen. Thereby, even if the meniscus 100 moves on the screen, the imaginary resection line 62 and imaginary freshening line 63 follow the movement, and the line positions on the meniscus 100 are maintained. In the meantime, since the resection line 61 in the first marking method is the marking which directly scars the meniscus 100, it is not preferable to re-draw the resection line 61. However, since the imaginary resection line 62 and imaginary freshening line 63 are drawn on the image of the meniscus 100, re-drawing is easy. In the description below, the resection line 61 and freshening line 57a and the imaginary resection line 62 and imaginary freshening line 63 are identical in function with respect to the distinction and determination of areas.

In the case of the horizontal tear 57, the imaginary resection line 62 is drawn in a manner to extend along the tear surface on the lower side (tibia 53 side) and to then obliquely rise from an intermediate point of the tear along the area B, and thus the resection target area 100c is set. Here, as illustrated in FIG. 4A, FIG. 4B and FIG. 4C, a tear site with a thickness t3 is resected from the meniscus 100 with an initial thickness t1 in which the horizontal tear 57 occurs. Thus, the thickness of the meniscus 100 after the resection decreases to a thickness t2.

As regards the setting of the imaginary resection line 62, it is important to obliquely set the imaginary resection line 62 so that no corner portion occurs on the upper surface of the meniscus 100 which will come in contact with the lower curved surfaces of the medial condyle of the femur and the lateral condyle of the femur after the completion of the treatment. By the formation of an oblique resection surface 100d, concentration of stress can be prevented when the upper surface of the meniscus 100 comes in contact with the femur.

Next, using the ultrasonic treatment tool 2, freshening treatment is performed on surfaces which become repair surfaces in the horizontal tear 57. As illustrated in FIG. 5, the treatment unit 14 of the ultrasonic treatment tool 2 is inserted into the remaining horizontal tear 57 from the upper surface 100c of the meniscus 100, and surface portions of the tear surfaces 57, which become repair surfaces, are shallowly resected and planarized with irregularities being eliminated, and microbleeding 101 is caused. This microbleeding may be caused by resecting surface portions of the tear surfaces 57 by the ultrasonic treatment tool 2, or may be caused by making a plurality of small holes in the surfaces.

Next, as a second example, a description is given of ultrasonic resection treatment at a time when a transverse tear 56 reaching the blood flow area A of the meniscus 100 occurred.

Figure 6A:
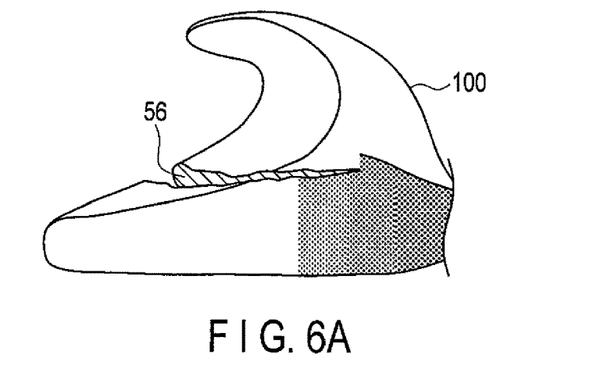
FIG. 6A is a cross-sectional view which conceptually illustrates a state in which a transverse tear occurred in the meniscus.
Figure 6B:
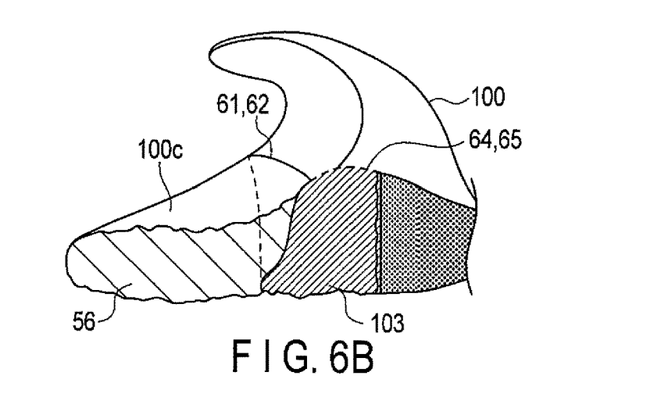
FIG. 6B is a cross-sectional view which conceptually illustrates a state in which an imaginary resection line is provided on the transverse tear.
Figure 6C:
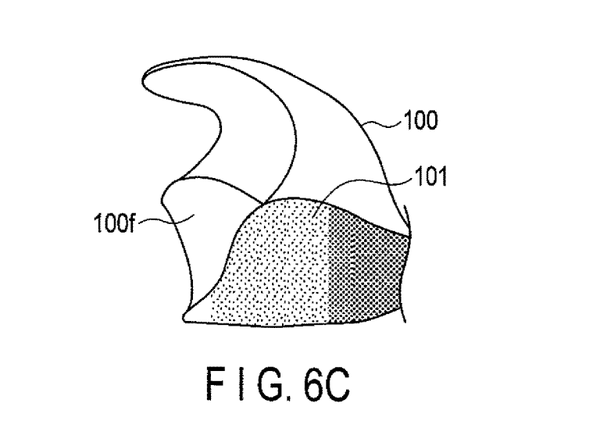
FIG. 6C is a cross-sectional view which conceptually illustrates a treatment state in which a repair surface is freshened.
Figure 6D:
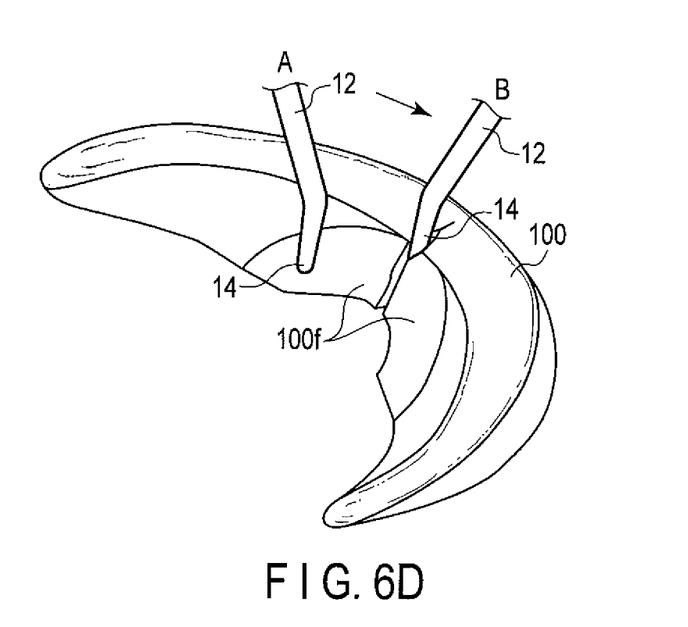
FIG. 6D is a view illustrating a state in which a tear site is resected by the ultrasonic treatment tool, and treatment for freshening is performed.

FIG. 6A is a cross-sectional view which illustrates a state in which a transverse tear 56 occurred in the meniscus 100. FIG. GB is a conceptual view illustrating an imaginary resection line being provided on the transverse tear 56. FIG. 6C is a cross-sectional view which conceptually illustrates a treatment state in which a repair surface is freshened. FIG. 6D is a view illustrating a state in which a tear site is resected by the ultrasonic treatment tool 2, and treatment for freshening is performed.

As illustrated in FIG. 6A, a transverse tear 56 by a tear in an up-and-down direction, which reaches the blood flow area A, occurs in a direction toward the inside from the no-blood-flow area C on the inside of the meniscus 100. Probing (identification of tear site) is performed in the meniscus 100.

To begin with, using the administering unit 8, a fluorescent medicine (ICG) is administered into a vein of a patient. Then, the arthroscope 21 is inserted, and excitation light is radiated from the excitation light source 23 to the meniscus 100. By the radiation of excitation light, the fluorescent medicine, which is diffused in the meniscus 100, emits fluorescence, as described in the above-described first example.

The surgeon selects either a first method or a second method. The first method is a direct drawing method in which the resection line 61 is marked by abutting the treatment unit 14, which generates ultrasonic vibrations, upon the meniscus. The second method is an imaginary drawing method in which the surgeon traces over the touch panel by the fingertip while viewing an IR image, thereby marking the imaginary resection line 62 on the display screen.

In the first method, the surgeon puts the treatment unit 14 of the ultrasonic treatment tool 2, which is caused to generate ultrasonic vibrations, into contact with the inner side end of the meniscus 100, while viewing the IR image under excitation light. Then, the surgeon moves the treatment unit 14 to a location in front of the blood flow area A (vascular area), and directly makes marking on the meniscus 100 (makes a scar in the shape of a thread or dots), thus drawing the resection line 61 and identifying a resection target area 100c. At this time, the resection line 61 is drawn in a manner to form an inclined surface beyond the transverse tear 56.

Next, a freshening line 64 is marked up to an end of the transverse tear 56 in the blood flow area A, and a freshening treatment area 103, which becomes a repair surface, is set. In addition, in FIG. 6C, the freshening treatment area 103 is a surface with no irregularities, which is planarized by the ultrasonic treatment tool 2, and microbleeds 101 occur on this surface. In these markings, it is preferable that the resection line 61 and freshening line 64 have different shapes so that the resection target area 100c and freshening treatment area can be visually distinguished.

In the second method, the surgeon traces over the meniscus image on which the blood flows are displayed with emphasis, and draws and inputs an imaginary resection line 26, as shown in FIG. 6B, from the touch panel. Thereby, the surgeon identifies a three-dimensional resection target area 100c. Next, the surgeon draws an imaginary freshening line 65 up to the end of the transverse tear 56, and sets a freshening treatment area 103. When this imaginary resection line 62 is drawn, the imaginary resection line 62 is set such that, after the resection, there remains no transverse tear 56 on the lower side of the meniscus 100 which comes in contact with the tibia 53, and a resection surface 100f has an inclination as described above.

In FIG. 6D, by using the ultrasonic treatment tool 2, the treatment unit 14 of the probe 12, which generates ultrasonic vibrations, is abutted upon the resection target area 100c, and the resection target area 100c is resected, thus forming the resection surface 100f. Thereafter, the treatment unit 14 is inserted in the transverse tear 56, and freshening treatment is performed for freshening the freshening treatment area 103 which becomes the repair surface.

Next, the procedure of treatment of the meniscus using the ultrasonic treatment tool is described.

Figure 6E:
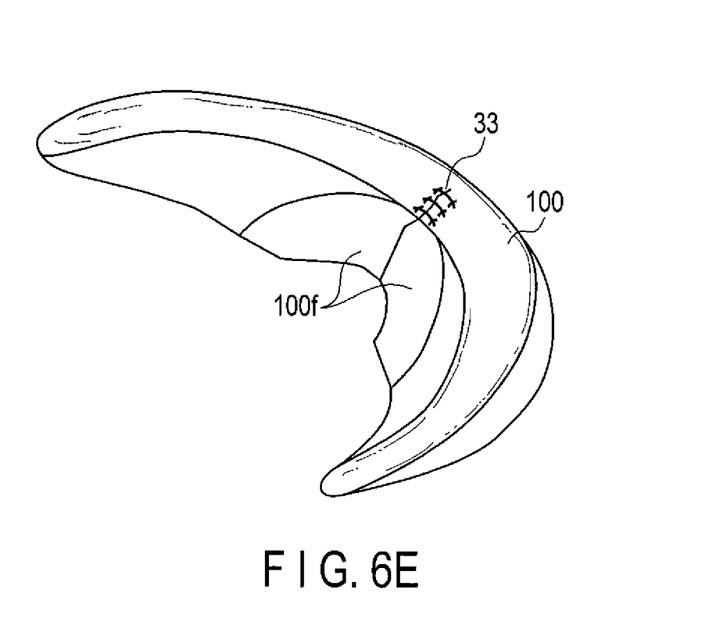
FIG. 6E is a view illustrating a state in which freshening treatment areas were joined and repair treatment is performed.
Figure 7:
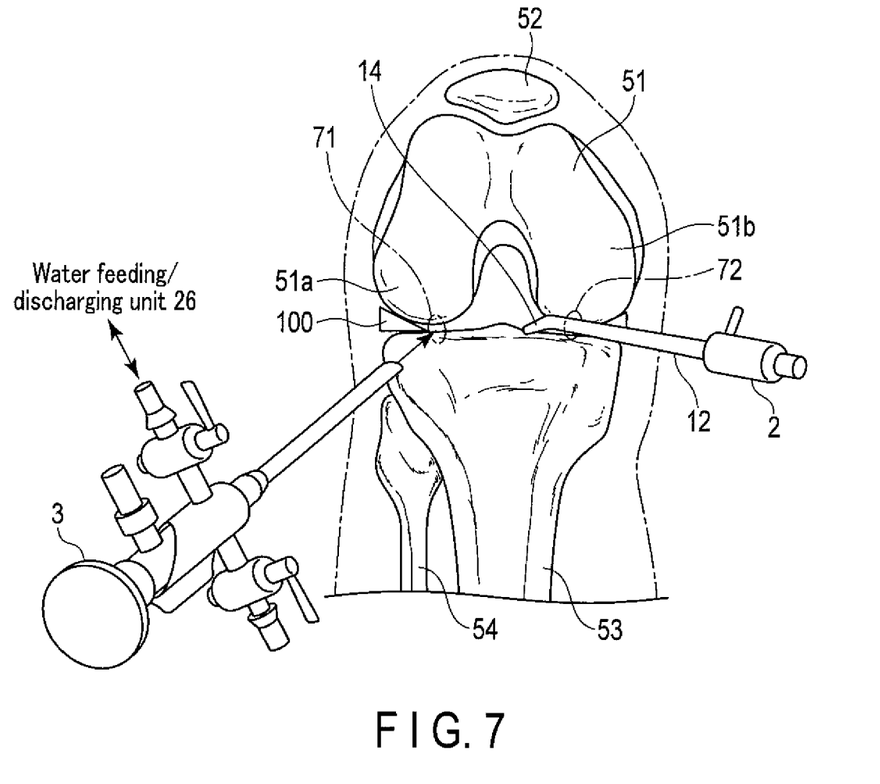
FIG. 7 is a view which conceptually illustrates a state of surgery in which an arthroscope and the ultrasonic treatment tool are inserted.
Figure 8A:
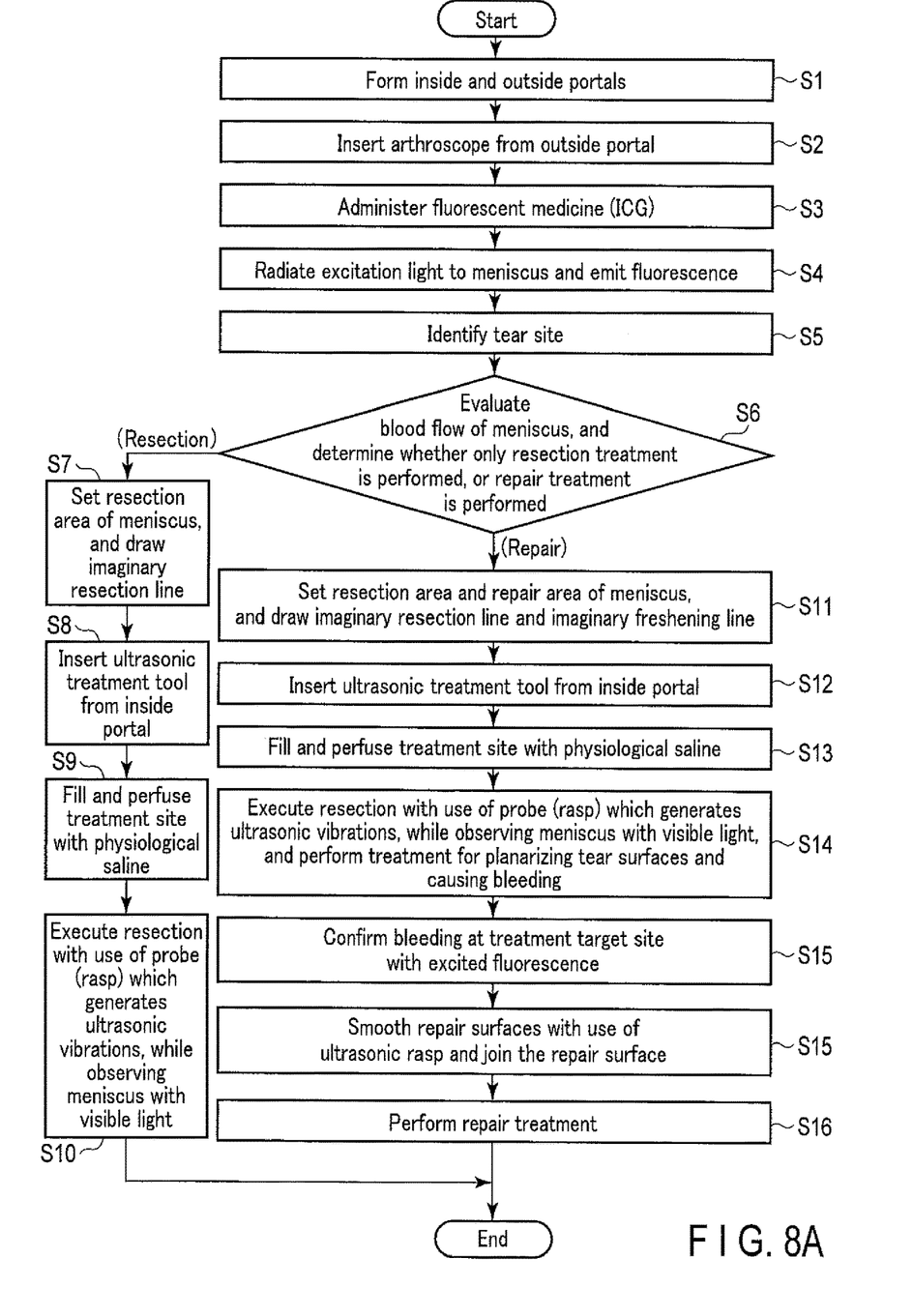
FIG. 8A is a flowchart for describing a first procedure of repair treatment of a meniscus.

Here, FIG. 7 is a view which conceptually illustrates a state of surgery in which an arthroscope and the ultrasonic treatment tool are inserted. FIG. 8A is a flowchart for describing a first procedure of resection and repair treatment of the meniscus. Here, repair treatment of the transverse tear illustrated in FIG. 6A to FIG. 6E is described by way of example. FIG. 6E illustrates the meniscus on which repair treatment is performed. FIG. 8A illustrates surgery steps of resection and repair treatment, in which no fluorescent medicine is administered to the articular cavity, a fluorescent medicine is administered into a vein, and an imaginary resection line is set on the image of the meniscus 100.

To start with, as illustrated in FIG. 7, a lateral parapatellar portal 71 (hereinafter referred to as "outside portal") for inserting the arthroscope 21 and a medial parapatellar portal 72 (hereinafter referred to as "inside portal") for inserting the ultrasonic treatment tool 2 are formed between the lower sides of the lateral condyle 51a and medial condyle 51b and the meniscus 100 of the bent knee of the patient (step S1). The arthroscope 21 is inserted from the outside portal 71 (step S2), and a fluorescent medicine (ICG) is administered to the vein of the patient by using the administering unit 8 (step S3). By radiating excitation light from the excitation light source 23, fluorescence is caused to occur, and the blood vessel and blood flow information in the meniscus 100 are displayed with emphasis on the display unit (step S4).

Next, probing (identification of tear site) is performed for the meniscus 100 which is displayed with emphasis on the display unit 28 (step S5). By this probing, if a transverse tear 56 as shown in FIG. 6A is identified, the blood flow in the meniscus is evaluated from the image of the meniscus 100, and the form and size of the tear, and the denaturing of the meniscus are examined. Thus, it is determined whether repair treatment is performed, or only resection treatment is performed (step S6).

In this determination, if it is determined that only resection treatment is performed, marking is made by drawing an imaginary resection line 62 (or resection line 61) as shown in FIG. 6B, and a resection target area 100c of the meniscus 100 is set three-dimensionally (step S8). In the meantime, as described above, the imaginary resection line 62 is drawn such that marking is made on the screen by tracing over the touch panel of the screen of the display unit 28 by the fingertip. In addition, the resection line 61 is drawn by directly marking a line on the meniscus 100 by the ultrasonic treatment tool 2.

Next, the surgeon inserts the ultrasonic treatment tool 2 from the inside portal 72 (step S8). Thereafter, perfusion water for articulation surgery is fed and perfused from the water feed/discharge unit 26 through the arthroscope 21, up to a state in which the periphery of the treatment site is filled with the perfusion water (step S9). While confirming the treatment site by viewing the observation image, the resection target area 100c of the meniscus 100 is resected by the treatment unit 14 (rasp) at the distal end of the probe 12 which is caused to generate ultrasonic vibrations (step S10).

In this resection treatment, resection is made such that the inclined surface 100f, which is cut obliquely downward from the upper surface, is formed. Conventionally, since the resection target area is perpendicularly resected by using a treatment tool such as a punch, a corner portion occurred at a location of the meniscus, upon which the femur abuts. If the femur abuts upon this corner portion, stress concentrates, leading to a factor which may cause new problems. Thus, the resection target area is obliquely resected and the oblique, planar surface is formed, so as to disperse the stress acting from the femur.

In addition, in step S6, when it is determined that the repair treatment is performed, marking is made by drawing the imaginary resection line 62 and imaginary freshening line 65 as illustrated in FIG. 6B, and the resection target area 100c and freshening treatment area 103 of the meniscus 100 are set three-dimensionally (step S11).

After the setting, the surgeon inserts the ultrasonic treatment tool 2 from the inside portal 72 (step S12), and feeds and perfuses perfusion water for articulation surgery from the water feed/discharge unit 26 through the arthroscope 21, up to a state in which the periphery of the treatment site is filled with the perfusion water (step S13). While confirming the position of the treatment site by viewing the observation image displayed on the display unit 28, the resection target area 100c is resected by abutting the treatment unit 14 at the distal end of the probe 12, which is caused to generate ultrasonic vibrations, upon the to-be-resected part of the meniscus. Further, the freshening treatment area 103 is planarized, with irregularities being eliminated, by the ultrasonic treatment tool 2, and the repair surface is formed and microbleeding 101 is caused on the surface (step S14). By making switching to excitation light, the microbleeding 101 is confirmed by the excited fluorescence (step S15).

After the confirmation, as illustrated in FIG. 6E, the freshening treatment areas 103, which are repair surfaces, are joined, and repair treatment is performed by a repair thread 33 (step S16).

In the meantime, if the tear site of the longitudinal tear 55, which extends in the up-and-down direction (longitudinally) along the longitudinal direction shown in FIG. 3D, is in the blood flow area A, B, the tear surfaces are planarized as the freshening treatment areas by the ultrasonic treatment tool 2, and bleeding is caused to occur, and the planarized surfaces are joined and repaired as repair surfaces. Besides, in the case of the flap tear 58 which is torn in the L shape, the part reaching the no-blood-flow area C is subjected to resection treatment to form an inclined surface, and the tear surfaces of the part reaching the blood flow area A or B is planarized as the freshening treatment areas by the ultrasonic treatment tool 2, and hemorrhage is caused, and the planarized surfaces are joined and repaired as repair surfaces.

Figure 8B:
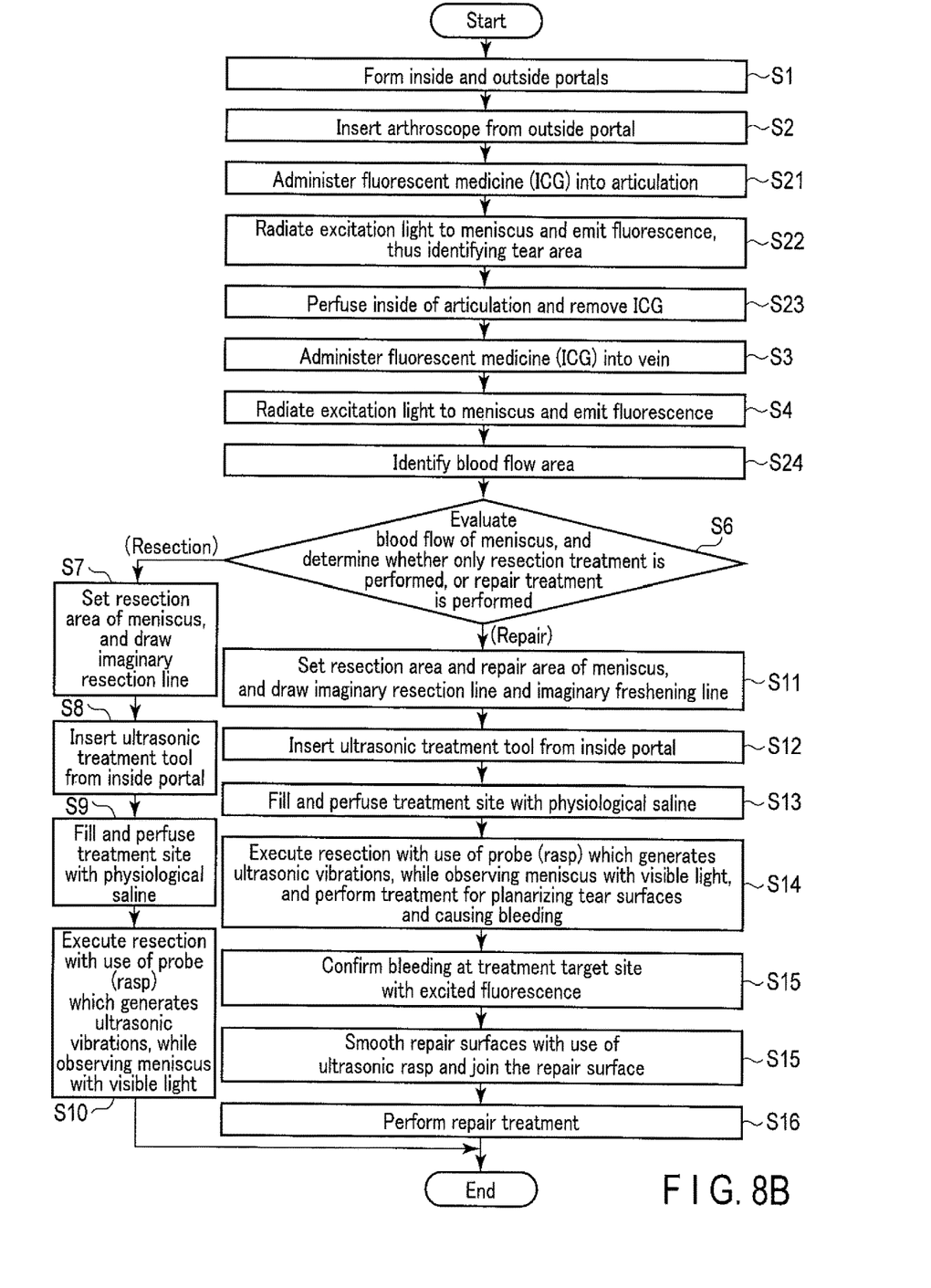
FIG. 8B is a flowchart for describing a second procedure of the repair treatment of the meniscus.

Next, a modification is described. FIG. 8B is a flowchart for describing a second procedure of the resection and repair treatment of the meniscus. FIG. 8B illustrates surgery steps of resection and repair treatment, in which a fluorescent medicine is administered to the articular cavity, a fluorescent medicine is administered into a vein, and an imaginary resection line is set on the image of the meniscus 100. Incidentally, in the description below, the surgery steps, which are identical in treatment content to the above-described surgery steps of FIG. 8A, are denoted by the same reference numerals of surgery steps, and a detailed description thereof is omitted. In the description below, since the drawings are referred to, the arthroscope 21 is inserted in the outside portal 71, and the ultrasonic treatment tool 2 is inserted in the inside portal 72. However, the respective positions of insertion are not restricted, and vary depending on the position of the treatment target.

To start with, two portals 71 and 72 for inserting the arthroscope 21 and ultrasonic treatment tool 2 are formed (step S1). The arthroscope 21 is inserted from the outside portal 71 (step S2). Thereafter, a fluorescent medicine (ICG) is administered into the articulation (step S21). By radiating excitation light to the meniscus 100, fluorescence is caused to occur, and a tear site is identified (step S22). After the identification, the inside of the articulation is perfused with perfusion water from the water feed/discharge unit 26 through the arthroscope 21, and the fluorescent medicine (ICG) is discharged and removed (step S23).

Next, using the administering unit 8, the fluorescent medicine (ICG) is administered to the vein of the patient (step S3). By radiating excitation light from the excitation light source 23, fluorescence is caused to occur, the blood vessel and blood flow information in the meniscus 100 is displayed with emphasis on the display unit 28, and the blood flow area is identified (step S24).

Next, the blood flow in the meniscus is evaluated from this blood flow area, and the form and size of the tear, and the denaturing of the meniscus are examined. Thus, it is determined whether repair treatment is performed, or only resection treatment is performed (step S6). In this determination, if it is determined that only resection treatment is performed, marking is made by drawing an imaginary resection line 62 (or resection line 61) as shown in FIG. 6B, and a resection target area 100c of the meniscus 100 is set three-dimensionally (step S7), and the surgeon inserts the ultrasonic treatment tool 2 from the inside portal 72 (step S8). Thereafter, perfusion water for articulation surgery is perfused and circuited (step S9), and the resection target area 100c is resected by the probe 12 which is caused to generate ultrasonic vibrations (step S10).

In addition, in step S6, when it is determined that the repair treatment is performed, marking is made by drawing the imaginary resection line 62 and imaginary freshening line 65, and the resection target area 100c and freshening treatment area 103 of the meniscus 100 are set three-dimensionally (step S11). After the setting, the surgeon inserts the ultrasonic treatment tool 2 (step S12), perfuses perfusion water for articulation surgery (step S13), resects the resection target area 100c by the probe 12 which is caused to generate ultrasonic vibrations, causes microbleeding 101 on the freshening treatment area 103 (step S14), and confirms the microbleeding 101 by the excited fluorescence (step S15). After the confirmation, the freshening treatment areas 103, which are repair surfaces, are joined, and repair treatment is performed by a repair thread 33 (step S16).

The arthroendoscopical surgical method of the above-described embodiment has the following advantageous effects.

In the arthroendoscopical surgical method of the embodiment, the fluorescent medicine (ICG) is administered to the blood flow of the patient, and the blood flow area (vascular area) of the meniscus 100, which emits fluorescence, can be confirmed, and it is possible to realize the setting of the resection target area 100c by the exact resection line, and the setting of the freshening treatment area on which microbleeding is caused.

The imaginary resection line, which is set under fluorescence, is superimposedly displayed on the image of the meniscus 100 which is illuminated by visible light in the surgical environment. Thus, the actual resection target area can be easily understood. In addition, since the setting of the imaginary resection line can be made by simply tracing on the displayed observation image, the imaginary resection line can be set easily in a short time.

By using the ultrasonic treatment tool for resecting the resection target area 100c of the meniscus 100, an inclined surface with no irregularities can be formed, and the stress on the surface, upon which the femur is abutted, can be dispersed.

By using the ultrasonic treatment tool, the angle between abutment surfaces of the repair surfaces of the freshening treatment area 103 can be adjusted, and planar surfaces with no irregularities can be formed. The repair surfaces can be repaired in close contact, contributing to earlier coalescence.

The treatment unit, to which an end portion of the ultrasonic treatment tool is fixed, is caused to generate microvibration, thereby to perform resection treatment. Thus, the surgeon can adjust the amount of cutting by the degree of pushing of the treatment unit upon the resection part. The surgeon can freely adjust the amount of cutting, between the resection/abscission treatment with strong pushing, and the planarization treatment for planarizing the resection surface with weak pushing, and realizes efficient resection, abscission, etc. Since the speed of resection can be adjusted, a resection target area with even a complicated shape can be finely resected.

The cutting by the probe, which generates ultrasonic vibration, is not the treatment by a heat source such as by an electric scalpel. Thus, the treatment can be performed without raising the temperature of the treatment site, and thermal invasion can be prevented.

Cutting progresses in the direction in which the probe is pushed. This is different from the cutting in the axial direction by a rotary shaft, such as by an electric drill, or the cutting utilizing the periphery of a rotating drill, which may involve other parts. Compared to the adjustment of the cutting amount based on conventional manual adjustment, the adjustment is very easy, and the fatigue of the surgeon is alleviated.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An arthroendoscopical surgical method using an ultrasonic treatment tool, comprising:
   an identifying step of identifying a tear site of a meniscus which is observed by an arthroscope;
   an imaging step of administering a fluorescent medicine to a blood flow of the meniscus through a vein, and imaging the meniscus in which the blood flow is displayed with emphasis under excitation light;
   a confirmation step of confirming whether the tear site in an image of the imaged meniscus reaches a vascular area;
   a step of confirming a blood vessel in a depth direction from a tear surface of the tear site in the image of the imaged meniscus;
   a step of forming mutually opposed planar repair surfaces by cutting the tear surfaces of the tear site in the depth direction by an ultrasonic treatment tool, such that bleeding occurs from the blood vessel in an inside of the meniscus to the tear surfaces; and
   a repair step of joining and suturing the repair surfaces formed in the step of forming the repair surfaces.

2. The arthroendoscopical surgical method of claim 1, wherein the step of forming the repair surfaces includes forming the repair surfaces by cutting the tear surfaces in the depth direction by the ultrasonic treatment tool, thereby causing bleeding to occur.

3. The arthroendoscopical surgical method of claim 1, further comprising a step of marking on a boundary of a repair area identified in the identifying step.

4. The arthroendoscopical surgical method of claim 1, further comprising:
   a step of administering a fluorescent medicine into an articular cavity; and
   a step of identifying a tear site by observing the administered fluorescent medicine by fluorescence under excitation light.

5. An arthroendoscopical surgical method using an ultrasonic treatment tool, comprising:
   an identifying step of identifying a tear site of a meniscus which is observed by an arthroscope;
   an imaging step of administering a fluorescent medicine to a blood flow of the meniscus through an articulation, and imaging the meniscus in which the blood flow is displayed with emphasis under excitation light;
   a determination step of confirming whether mutually opposed tear surfaces of the tear site reach a vascular area in an image of the imaged meniscus, and determining whether resection treatment or repair treatment is performed;
   a setting step of setting, when the tear surfaces of the tear site do not reach the vascular area in the determination step, a resection target area by drawing a resection line such that a resection surface including the tear site is obliquely inclined, and setting, when the tear site reaches the vascular area, a freshening treatment area, in addition to the setting of the resection target area, by drawing a freshening line for bleeding from a blood vessel at a part of the tear site reaching the vascular area;
   a formation step of resecting the resection target area set in the setting step by an ultrasonic treatment tool, thereby forming a planar, obliquely inclined resection surface which comes in contact with a femur, and also cutting the freshening treatment area by the ultrasonic treatment tool, thereby forming planar repair surfaces with bleeding; and
   a repair step of joining and suturing the repair surfaces formed in the formation step.

6. The arthroendoscopical surgical method of claim 5, wherein the resection line and the freshening line in the setting step are drawn on the meniscus by a probe of the ultrasonic treatment tool, the probe being configured to generate ultrasonic vibrations.

7. The arthroendoscopical surgical method of claim 5, wherein the resection line and the freshening line in the setting step are drawn by causing a display screen, which is equipped with a touch panel, to display an image of the imaged meniscus, and marking an imaginary resection line, through the touch panel, on the resection target area and the freshening treatment area which are displayed, in association with positional information of the image of the meniscus.

8. The arthroendoscopical surgical method of claim 5, wherein the repair step includes forming the tear surfaces by cutting the tear surfaces in a depth direction by the ultrasonic treatment tool, and causing bleeding to occur.

9. The arthroendoscopical surgical method of claim 5, further comprising:
   a step of administering a fluorescent medicine into an articular cavity; and
   a step of identifying a tear site by observing the administered fluorescent medicine by fluorescence under excitation light.

* * * * *